(12) United States Patent
Scheiflinger et al.

(10) Patent No.: US 7,763,430 B2
(45) Date of Patent: Jul. 27, 2010

(54) DIAGNOSTIC ASSAY FOR ANTI-VON WILLEBRAND FACTOR CLEAVING PROTEASE (ADAMTS13) ANTIBODIES

(75) Inventors: Friedrich Scheiflinger, Vienna (AT); Manfred Rieger, Gaenserndorf (AT); Barbara Plaimauer, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 304 days.

(21) Appl. No.: 10/422,052

(22) Filed: Apr. 22, 2003

(65) Prior Publication Data

US 2004/0214346 A1    Oct. 28, 2004

(51) Int. Cl.
*G01N 33/53* (2006.01)
(52) U.S. Cl. ...................................... 435/7.1; 435/90.1
(58) Field of Classification Search ................... 435/7.1, 435/7.2, 7.92
See application file for complete search history.

(56) References Cited

U.S. PATENT DOCUMENTS 6,008,335 A * 12/1999 Rotter et al. ............... 536/23.1
2003/0228284 A1 * 12/2003 McCown et al. ........... 424/93.2

FOREIGN PATENT DOCUMENTS

WO    WO 02/42441 A2    5/2002

OTHER PUBLICATIONS

Additivity of Mutational Effects in Proteins. Biochemistry 29(37): 8509-8517.*
The Protein Folding Problem and Tertiary Structure Prediction, Chapter 14: Computational Complexity Protein Structure Prediction, and the Levinthal Paradox pp. 492-495.*
Smith and Zhang (Nov. 1997) The challenges of genome sequence annotation or 'The devil is in the details'.*
Brenner (Apr. 1999) "Errors in genome annotation." Trends in Genetics 15(4): 132-133;).*
Tsai et al. (Ann. Intern Med. 2001 vol. 132, p. 794-799).*
Furlan, M. et al. "Acquired Deficiency of von Willebrand Factor-Cleaving Protease in a Patient With Thrombotic Thrombocytopenic Purpura", *Blood*, Apr. 15, 1998; pp. 2839-2846, vol. 91, No. 8.
Furlan, M. et al. "Assays of von Willebrand Factor-Cleaving Protease: A Test for Diagnosis of Familial and Acquired Thrombotic Thrombocytopenic Purpura", *Seminars in Thrombosis and Hemostasis*, 2002, pp. 167-172, vol. 28, No. 2.
Furlan, M. et al. "Partial Purification and Characterization of a Protease From Human Plasma Cleaving von Willebrand Factor to Fragments Produced by In Vivo Proteolysis", *Blood*, May 15, 1996; pp. 4223-4234, vol. 87, No. 10.
Furlan, M. et al. "Von Willebrand Factor-Cleaving Protease in Thrombotic Thrombocytopenic Purpura and the Hemolytic-Uremic Syndrome", *New England Journal of Medicine*, Nov. 26, 1998; pp. 1578-1584, vol. 339, No. 22.
Gerritsen, H et al. " Assays of von Willebrand Factor (vWF)-Cleaving Protease Based on Decreased Collagen Binding Affinity of Degraded vWF", *Thromb Haemost*, 1999, pp. 1386-1389, vol. 82.
Moake, J. "Thrombotic Microangiopathies", *New England Journal of Medicine*, Aug. 22, 2002; pp. 589-600, vol. 347, No. 8.
Zheng, X et al. "Structure of von Willebrand Factor-cleaving Protease (ADAMTS13), a Metalloprotease Involved in Thrombotic Thrombocytopenic Purpura", J Biological Chemistry, Nov. 2, 2001, pp. 41059-41063, vol. 276, No. 44, Printed in the U.S.A.

* cited by examiner

*Primary Examiner*—Jacob Cheu
(74) *Attorney, Agent, or Firm*—Townsend and Townsend and Crew LLP

(57) ABSTRACT

This invention relates to a kit to be used in an assay system for determination of an anti-von Willebrand Factor-cleaving protease ("anti-vWF-cp") antibody in a sample. The kit comprises vWF-cp and/or vWF-fragment(s) immobilized on a solid phase. The kit can be used in a method for determination of anti-vWF-cp antibodies from a patient, for the diagnosis of disorders associated with the occurrence of anti-vWF-cp-antibodies, and the differentiation of various forms of thrombotic microangiopathy.

7 Claims, 2 Drawing Sheets

SEQUENCE LISTING

<160> NUMBER OF SEQ ID NOS: 6

<210> SEQ ID NO 1
<211> LENGTH: 45
<212> TYPE: PRT
<213> ORGANISM: human

<400> SEQUENCE: 1

Pro Ser His Phe Gln Gln Ser Cys Leu Gln Ala Leu Glu Pro Gln Ala
1               5                  10                  15

Val Ser Ser Tyr Leu Ser Pro Gly Ala Pro Leu Lys Gly Arg Pro Pro
            20                  25                  30

Ser Pro Gly Phe Gln Arg Gln Arg Gln Arg Gln Arg Arg
        35                  40                  45

<210> SEQ ID NO 2
<211> LENGTH: 353
<212> TYPE: PRT
<213> ORGANISM: human

<400> SEQUENCE: 2

Ala Ala Gly Gly Ile Leu His Leu Glu Leu Leu Val Ala Val Gly Pro
1               5                  10                  15

Asp Val Phe Gln Ala His Gln Glu Asp Thr Glu Arg Tyr Val Leu Thr
            20                  25                  30

Asn Leu Asn Ile Gly Ala Glu Leu Leu Arg Asp Pro Ser Leu Gly Ala
            35                  40                  45

Gln Phe Arg Val His Leu Val Lys Met Val Ile Leu Thr Glu Pro Glu
        50                  55                  60

Gly Ala Pro Asn Ile Thr Ala Asn Leu Thr Ser Ser Leu Leu Ser Val
65                  70                  75                  80

Cys Gly Trp Ser Gln Thr Ile Asn Pro Glu Asp Asp Thr Asp Pro Gly
            85                  90                  95

His Ala Asp Leu Val Leu Tyr Ile Thr Arg Phe Lys Leu Glu Asp Pro
            100                 105                 110

Asp Gly Asn Arg Gln Val Arg Gly Val Thr Gln Leu Gly Gly Ala Cys
            115                 120                 125

Ser Pro Thr Trp Ser Cys Leu Ile Thr Glu Asp Thr Gly Phe Asp Leu
            130                 135                 140

Gly Cys Thr Ile Ala His Glu Ile Gly His Ser Phe Gly Leu Glu His
145                 150                 155                 160

Asp Gly Ala Pro Gly Ser Gly Cys Gly Pro Ser Gly His Val Met Ala
            165                 170                 175

Ser Asp Gly Ala Ala Pro Arg Ala Gly Leu Ala Trp Ser Pro Cys Ser
            180                 185                 190

Arg Arg Gln Leu Leu Ser Leu Leu Ser Ala Gly Arg Ala Arg Cys Val
            195                 200                 205

Trp Asp Pro Pro Arg Pro Gln Pro Gly Ser Ala Gly His Pro Pro Asp
            210                 215                 220

Ala Gln Pro Gly Leu Tyr Tyr Ser Ala Asn Glu Gln Cys Arg Val Ala
225                 230                 235                 240

Phe Gly Pro Lys Ala Val Ala Cys Thr Phe Ala Arg Glu His Leu Asp
            245                 250                 255

Met Cys Gln Ala Leu Ser Cys His Thr Asp Pro Leu Asp Gln Ser Ser
            260                 265                 270

Cys Ser Arg Leu Leu Val Pro Leu Leu Asp Gly Thr Glu Cys Gly Val
            275                 280                 285

Glu Lys Trp Cys Ser Lys Gly Arg Cys Arg Ser Leu Val Glu Leu Thr
            290                 295                 300

Pro Ile Ala Ala Val His Gly Arg Trp Ser Ser Trp Gly Pro Arg Ser
305                 310                 315                 320

Pro Cys Ser Arg Ser Cys Gly Gly Val Val Thr Pro Pro Pro Pro Gln
            325                 330                 335

Cys Asn Asn Pro Arg Pro Ala Phe Gly Gly Arg Ala Cys Val Gly Ala
            340                 345                 350

Asp

<210> SEQ ID NO 3
<211> LENGTH: 42
<212> TYPE: PRT
<213> ORGANISM: human

<400> SEQUENCE: 3

Arg Trp Ser Ser Trp Gly Pro Arg Ser Pro Cys Ser Arg Ser Cys Gly
1               5                   10                  15

Gly Gly Val Val Thr Pro Pro Pro Gln Cys Asn Asn Pro Arg Pro Ala
            20                  25                  30

Phe Gly Gly Arg Ala Cys Val Gly Ala Asp
            35                  40

<210> SEQ ID NO 4
<211> LENGTH: 247
<212> TYPE: PRT
<213> ORGANISM: human

<400> SEQUENCE: 4

Lys Thr Gln Leu Glu Phe Met Ser Gln Gln Cys Ala Arg Thr Asp Cys
1               5                   10                  15

```
Gln Pro Leu Arg Ser Ser Pro Gly Gly Ala Ser Phe Tyr His Trp Gly
             20                  25                  30

Ala Ala Val Pro His Ser Gln Gly Asp Ala Leu Cys Arg His Met Cys
         35                  40                  45

Arg Ala Ile Gly Glu Ser Phe Ile Met Lys Arg Gly Asp Ser Phe Leu
 50                  55                  60

Asp Gly Thr Arg Cys Met Pro Ser Gly Pro Arg Glu Asp Gly Thr Leu
 65                  70                  75                  80

Ser Leu Cys Val Ser Gly Ser Cys Arg Thr Phe Gly Cys Asp Cys Arg
                 85                  90                  95

Met Asp Ser Gln Gln Val Trp Asp Arg Cys Gln Val Cys Gly Gly Asp
            100                 105                 110

Asn Ser Thr Cys Ser Pro Arg Lys Gly Ser Phe Thr Ala Gly Arg Ala
        115                 120                 125

Arg Glu Tyr Cys Thr Phe Leu Thr Cys Thr Pro Asn Leu Thr Ser Cys
130                 135                 140

Tyr Ile Ala Asn His Arg Pro Leu Phe Thr His Leu Ala Val Arg Ile
145                 150                 155                 160

Gly Gly Arg Tyr Val Val Ala Gly Lys Met Ser Ile Ser Pro Asn Thr
                165                 170                 175

Thr Tyr Pro Ser Ile Leu Leu Glu Asp Gly Arg Val Glu Tyr Arg Val
            180                 185                 190

Ala Leu Thr Glu Asp Arg Leu Pro Arg Leu Glu Glu Ile Arg Ile Trp
        195                 200                 205

Gly Pro Leu Gln Glu Asp Ala Asp Ile Gln Val Tyr Arg Arg Tyr Gly
210                 215                 220

Glu Glu Tyr Gly Asn Leu Thr Arg Pro Asp Ile Thr Phe Thr Tyr Phe
225                 230                 235                 240

Gln Pro Lys Pro Arg Gln Ala
            245

<210> SEQ ID NO 5
<211> LENGTH: 444
<212> TYPE: PRT
<213> ORGANISM: human

<400> SEQUENCE: 5

Trp Val Trp Ala Ala Val Arg Gly Pro Cys Ser Val Ser Ser Gly Ala
 1               5                  10                  15

Gly Leu Arg Trp Val Asn Gln Ser Cys Leu Asp Gln Ala Arg Lys Glu
            20                  25                  30

Leu Val Glu Thr Val Gln Cys Gln Gly Ser Gln Gln Pro Pro Ala Trp
         35                  40                  45

Pro Glu Ala Cys Val Leu Glu Pro Cys Pro Tyr Trp Ala Val Gly
 50                  55                  60

Asp Phe Gly Pro Cys Ser Ala Ser Cys Gly Gly Gly Leu Arg Glu Arg
 65                  70                  75                  80

Pro Val Arg Cys Val Glu Ala Gln Gly Ser Leu Leu Lys Thr Leu Pro
                 85                  90                  95

Pro Ala Arg Cys Arg Ala Gly Ala Gln Gln Pro Ala Val Ala Leu Glu
            100                 105                 110

Thr Cys Asn Pro Gln Pro Cys Pro Ala Arg Trp Glu Val Ser Glu Pro
        115                 120                 125

Ser Ser Cys Thr Ser Ala Gly Gly Ala Gly Leu Ala Leu Glu Asn Glu
130                 135                 140
```

```
Thr Cys Val Pro Gly Ala Asp Gly Leu Glu Ala Pro Val Thr Glu Gly
145                 150                 155                 160

Pro Gly Ser Val Asp Glu Lys Leu Pro Ala Pro Glu Pro Cys Val Gly
                165                 170                 175

Met Ser Cys Pro Pro Gly Trp Gly His Leu Asp Ala Thr Ser Ala Gly
            180                 185                 190

Glu Lys Ala Pro Ser Pro Trp Gly Ser Ile Arg Thr Gly Ala Gln Ala
        195                 200                 205

Ala His Val Trp Thr Pro Val Ala Gly Ser Cys Ser Val Ser Cys Gly
    210                 215                 220

Arg Gly Leu Met Glu Leu Arg Phe Leu Cys Met Asp Ser Ala Leu Arg
225                 230                 235                 240

Val Pro Val Gln Glu Glu Leu Cys Gly Leu Ala Ser Lys Pro Gly Ser
                245                 250                 255

Arg Arg Glu Val Cys Gln Ala Val Pro Cys Pro Ala Arg Trp Gln Tyr
            260                 265                 270

Lys Leu Ala Ala Cys Ser Val Ser Cys Gly Arg Gly Val Val Arg Arg
        275                 280                 285

Ile Leu Tyr Cys Ala Arg Ala His Gly Glu Asp Asp Gly Glu Glu Ile
    290                 295                 300

Leu Leu Asp Thr Gln Cys Gln Gly Leu Pro Arg Pro Glu Pro Gln Glu
305                 310                 315                 320

Ala Cys Ser Leu Glu Pro Cys Pro Pro Arg Trp Lys Val Met Ser Leu
                325                 330                 335

Gly Pro Cys Ser Ala Ser Cys Gly Leu Gly Thr Ala Arg Arg Ser Val
            340                 345                 350

Ala Cys Val Gln Leu Asp Gln Gly Gln Asp Val Glu Val Asp Glu Ala
        355                 360                 365

Cys Ala Ala Leu Val Arg Pro Glu Ala Ser Val Pro Cys Leu Ile Ala
    370                 375                 380

Asp Cys Thr Tyr Arg Trp His Val Gly Trp Met Glu Cys Ser Val Ser
385                 390                 395                 400

Cys Gly Asp Gly Ile Gln Arg Arg Arg Asp Thr Cys Leu Gly Pro Gln
                405                 410                 415

Ala Gln Ala Pro Val Pro Ala Asp Phe Cys Gln His Leu Pro Lys Pro
            420                 425                 430

Val Thr Val Arg Gly Cys Trp Ala Gly Pro Cys Val
        435                 440

<210> SEQ ID NO 6
<211> LENGTH: 294
<212> TYPE: PRT
<213> ORGANISM: human

<400> SEQUENCE: 6

Gly Gln Gly Thr Pro Ser Leu Val Pro His Glu Glu Ala Ala Ala Pro
1               5                   10                  15

Gly Arg Thr Thr Ala Thr Pro Ala Ala Gly Ala Ser Leu Glu Trp Ser Gln
            20                  25                  30

Ala Arg Gly Leu Leu Phe Ser Pro Ala Arg Gln Pro Arg Arg Leu Leu
        35                  40                  45

Pro Gly Pro Gln Glu Asn Ser Val Gln Ser Ser Ala Cys Gly Arg Gln
    50                  55                  60

His Leu Glu Pro Thr Gly Thr Ile Asp Met Arg Gly Pro Cys Gln Ala
```

-continued

```
             65                  70                  75                  80
Asp Cys Ala Val Ala Ile Gly Arg Pro Leu Gly Glu Val Val Thr Leu
                 85                  90                  95

Arg Val Leu Glu Ser Ser Leu Asn Cys Ser Ala Gly Asp Met Leu Leu
            100                 105                 110

Leu Trp Gly Arg Leu Thr Arg Lys Met Cys Arg Lys Leu Leu Asp Met
            115                 120                 125

Thr Phe Ser Ser Lys Thr Asn Thr Leu Val Val Arg Gln Arg Cys Gly
            130                 135                 140

Arg Pro Gly Gly Gly Val Leu Leu Arg Tyr Gly Ser Gln Leu Ala Pro
145                 150                 155                 160

Glu Thr Phe Tyr Arg Glu Cys Asp Met Gln Leu Phe Gly Pro Trp Gly
            165                 170                 175

Glu Ile Val Ser Pro Ser Leu Ser Pro Ala Thr Ser Asn Ala Gly Gly
            180                 185                 190

Cys Arg Leu Phe Ile Asn Val Ala Pro His Ala Arg Ile Ala Ile His
            195                 200                 205

Ala Leu Ala Thr Asn Met Gly Ala Gly Thr Glu Gly Ala Asn Ala Ser
            210                 215                 220

Tyr Ile Leu Ile Arg Asp Thr His Ser Leu Arg Thr Thr Ala Phe His
225                 230                 235                 240

Gly Gln Gln Val Leu Tyr Trp Glu Ser Glu Ser Ser Gln Ala Glu Met
            245                 250                 255

Glu Phe Ser Glu Gly Phe Leu Lys Ala Gln Ala Leu Arg Gly Gln Tyr
            260                 265                 270

Trp Thr Leu Gln Ser Trp Val Pro Glu Met Gln Asp Pro Gln Ser Trp
            275                 280                 285

Lys Gly Lys Glu Gly Thr
            290
```

DIAGNOSTIC ASSAY FOR ANTI-VON WILLEBRAND FACTOR CLEAVING PROTEASE (ADAMTS13) ANTIBODIES

FIELD OF THE INVENTION

This invention relates to a kit to be used in an assay system for determination of an anti-von Willebrand Factor-cleaving protease (ADAMTS13) antibody ("anti-vWF-cpantibody") in a sample suspected to comprise an anti-vWF-cp antibody. The kit can be used in a method for diagnosis of disorders associated with the occurrence of anti-vWF-cp-antibodies in patients, and to discriminate between different forms of thrombotic microangiopathy.

BACKGROUND OF THE INVENTION

One important protein in primary hemostasis is von Willebrand Factor (vWF). Plasma von Willebrand Factor (vWF) is a multimeric protein that mediates adhesion of platelets to sites of vascular injury, and especially the very large vWF multimers are haemostatically competent. The existence of plasma factors that control the size of vWF multimers has long been suspected. The von Willebrand Factor-cleaving protease ("vWF-cp") is involved in the limitation of platelet thrombus growth by proteolytic cleavage of von Willebrand Factor multimers in man (Furlan et al., (1996) Blood 87: 4223-4234). Recently, the molecular structure of von Willebrand Factor-cleaving protease and the corresponding gene have been described (WO 02/42441; Zheng et al., (2001) J. Biol. Chem. 276: 41059-41063) and have been identified as a new member of the ADAMTS family and designated ADAMTS 13. vWFcp regulates vWF multimer size by proteolytic cleavage.

The large and ultra large vWF multimers play a central role in arterial thrombosis, whereby unusually large mutlimers of vWF have been seen in two similar forms of thrombotic microangiopathy—thrombotic thrombocytopenic purpura (TTP) and hemolytic-uremic syndrome (HUS)—both resulting in formation of platelet aggregation leading to disseminated occlusions in the microcirculation. Patients with TTP have a deficiency of vWF-cp, whereas patients with HUS show normal activity of the protease.

There are several types of TTP: An acute idiopathic or sporadic form, an intermittent form with an eventual relapse, and a chronic relapsing form. Chronic relapsing TTP is associated with acquired or congenital deficiency of vWF-cp. The rare hereditary form of TTP has been related to specific gene mutations in the ADAMTS-13 locus. Acute idiopathic TTP or acquired TTP is usually more severe than chronic relapsing TTP, wherein these patients have acquired antibodies against vWF-cp, which inhibit the von Willebrand Factor-cleaving protease (Furlan et al., (1998) Blood 91: 2839-2846; Furlan et al., (1998) N. Engl. J. Med. 339: 1578-1584). Acquired TTP also occurs occasionally during pregnancy or in the postpartum period. Intermittent relapsing TTP is also associated with the reappearance of vWF-cp inhibitor. For other forms of TTP, such as ticlopidine-associated TTP, it has also been observed that these patients have acquired antibodies against vWF-cp (Moake, (2002) N. Eng. J. Med. 347:589-600). However, some patients with acquired TTP having unusually large vWF multimers in plasma lack severe reduced levels of vWF-cp.

In general, inhibitory antibodies against proteins cause serious problems, for example within the coagulation cascade, leading to blood loss or thrombosis.

Congenital and acquired TTP are discriminated by the presence of inhibitory antibodies against vWF-cp in the plasma of up to 80% of patients suffering from acquired TTP, and total absence of vWF-cp in plasma of patients with hereditary TTP. So far, inhibitory antibodies in plasma of patients are determined by static enzyme assays under non-physiological conditions and confirm the diagnosis of acute, antibody-mediated TTP.

Different assays of vWF-cp for diagnosis of congenital and acquired TTP have been described. vWF-cp activity and the presence of inhibitors of vWF-cp are determined by incubation of purified vWF multimers with plasma samples of patients, followed by immunoblotting of degraded vWF substrate with anti-vWF antibodies and multimer analysis (Furlan et al., (2002) Sem. Thromb. Haemost. 28:167-172). The method is very sensitive in the range of low protease activity; however, the accuracy is only moderate in the subnormal or normal range of protease activity. A collagen-binding assay for determination vWF-cp activity and vWF-cp inhibitors as described by Gerritsen et al. [(1999) Thromb. Haemost. 82:1386-1389] can be completed within 6 hours, but the method is less sensitive in the very low range of protease activity as compared to the immunoblotting of degraded vWF multimers (Furlan et al. 2002 supra). The assays described in the prior art, however, are very cumbersome, time consuming and require the expertise of laboratories familiar with the technique. Moreover, the known prior art assays only allow for detection of vWF-cp inhibitors that impair the catalytic function of vWF-cp. Inhibitory antibodies which may impair a vWF-cp function other than the catalytic activity, e.g. endothelial cell binding, cannot be detected by these assays.

Therefore a need exists for a test system that allows the detection and determination of anti-vWF-cp antibodies in a patient's plasma that impair vWF-cp function other than the enzyme's catalytic protease activity.

SUMMARY OF THE INVENTION

An object of the present invention is to provide a kit for determination of an anti-vWF-cp antibody in a sample. The kit comprises vWF-cp and/or one or more vWF-cp fragment(s) immobilized on a solid phase without substantially impairing the biological property of the vWF-cp or vWF-cp-fragment(s). Additionally, the kit of the present invention may also contain any auxiliary agents known in the art for carrying out antigen/antibody assays (e.g., ELISA, EIA, RIA etc.), such as buffer salts, buffer disclosed solutions, blocking agents, detecting agents and the like. The kits that are disclosed can be provided in a variety of formats, e.g., in the form of one or more containers or a microtiter plate.

Surprisingly, the inventors have found that vWF-cp or a vWF-cp fragment immobilized on a solid phase provides a simple, efficient, fast and reproducible assay system for determination of the presence of an anti-vWF-cp antibody in a sample. With the system of the present invention, vWF-cp inhibitors have been determined which were not detected in a system of the prior art. The kit of the present invention provides an increased sensitivity in the current assay than prior art assays and can be used to detect vWF-antibodies amounts that may be below the detection limit of known systems. Assays performed with the kit of present invention allows one to discriminate between anti-vWF-cp antibodies having different specificities and based on impairment of different biological functions of vWF-cp. The assay to be performed with the kit of the present invention further allows for a rapid diagnosis of TTP and other disorders associated with vWF-cp inhibitors, as well as differentiation of various forms of thrombotic microangiopathy (TM).

DETAILED DESCRIPTION OF THE INVENTION

Figure 1:
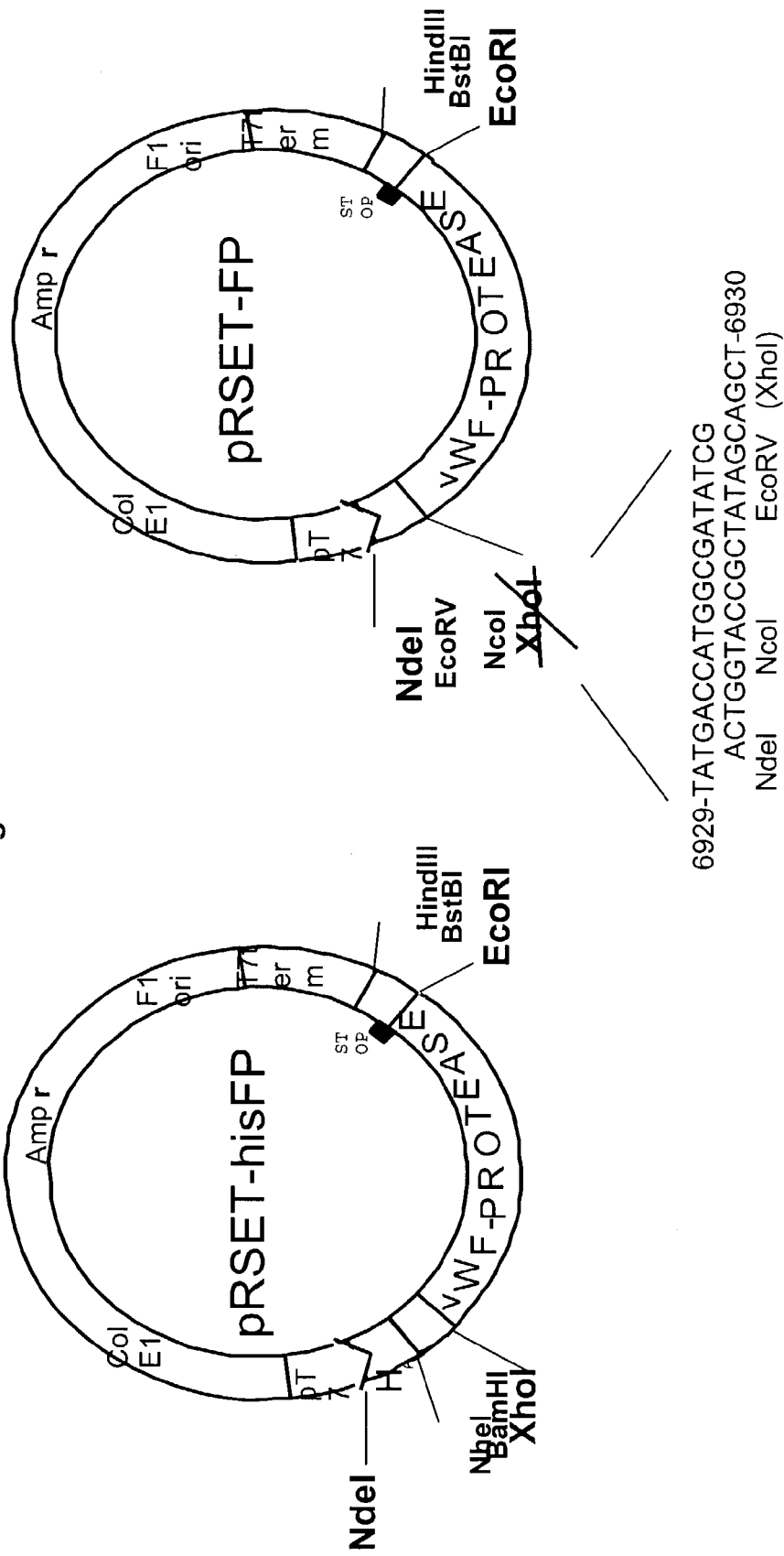
FIG. 1 shows examples of plasmids that can be used for expression of recombinant vWF-cp, vWF-cp-fragment(s), or vWF-cp or vWF-cp-fragment(s) fused to a his-tag heterologous sequence.

One aspect of the invention relates to a kit for determination of an anti-vWF-cp antibody in a sample comprising vWF-cp and/or a vWF-cp fragment immobilized on a solid phase without substantially impairing the biological property of the vWF-cp or the vWF-cp fragment. The vWF-cp or vWF-cp-fragment is used in the kit as diagnostic agent providing the antigenic determination site(s) capable of binding anti-vWF-cp-antibodies present in a sample.

The term "determination" as used herein is meant to include detection, quantification and mapping of the vWF-cp antigen-binding region of an anti-vWF-cp-antibody in a sample. "Detection" means at least one positive reaction indicating the formation of an antibody/vWF-cp—or an antibody/vWF-cp fragment—complex with a detection system, e.g., a chromogenic assay. A sample known not to comprise any anti-vWF-antibody, e.g., normal human plasma is used as negative control. "Quantification" typically means that defined dilutions of a sample suspected to comprise anti-vWF-cp antibodies are contacted with the immobilized vWF-cp or a vWF-cp fragment, and the intensity of the reaction obtained by the detection system is compared to the intensity of the reaction obtained with defined dilutions of a sample comprising a known and defined amount of anti-vWF-antibodies, which is used as a standard. "Mapping" of the vWF-cp antigen binding site of an anti-vWF-cp antibody is performed by contacting the sample suspected to comprise anti-vWF-cp antibodies with complete vWF-cp as well as with vWF-cp fragments derived from different regions of the vWF-cp molecule. Thereby, the complete spectrum of anti-vWF-cp antibodies possibly present in a sample can be captured and anti-vWF-cp antibodies having specific binding activity within a region/domain of vWF-cp can be identified.

The term "sample" as used herein is meant to refer to a biological fluid such as blood, plasma or tissue of a patient. The sample may be in particular obtained from human patients suspected of having a disorder associated with occurrence of anti-vWF-cp antibodies The term "solid phase" does not imply any specific limitations, and relates, for example, to an unsoluble polymer material, which can be an organic polymer, such as polyamide or a vinyl polymer (e.g., poly(meth)acrylate, polystyrene and polyvinyl alcohol, or derivates thereof), a natural polymer such as cellulose, dextrane, agarose, chitin and polyamino acids, or an inorganic polymer, such as glass or metallohydroxide. The solid phase can be in the form of a microcarrier, particles, membranes, strips, paper, film, pearls or plates, such as microtiter plates. The vWF-cp or vWF-cp fragment(s) can be immobilized on the solid phase directly by covalent coupling or via a carrier such as a linker molecule or an antibody immobilized on the solid phase.

The term "biological property" as used herein is meant as functionally active epitopes or antigenic determinants of vWF-cp or the vWF-cp fragments, capable of binding at least one anti-vWF-cp antibody. The immobilization of vWF-cp or vWF-cp fragment on a solid phase is performed in such a way that the immunologic properties, in particular the structure of the functional epitopes and antigenic determinants of vWF-cp or the vWF-cp fragments are preserved and efficiently presented to be recognized by at least one anti-vWF-cp antibody present in the sample.

The vWF-cp or vWF-cp fragments can be produced in whole or in part by recombinant techniques and can be prepared by expression in a prokaryotic or eukaryotic host system. Prokaryotic hosts can be bacterial cells such as *E. coli* or *B. subtilis*. Eukaryotic cells can be selected from the group consisting of yeast cells (e.g., *Pichia* strains); insect cells (e.g., Sf9, Sf 21, High Five, S2); and mammalian cells, such as MRC5, CHO, COS, 3T3, HEK 293, BHK, SK-Hep, HepG2, CV-1, and Hela.

A wide variety of vectors can be used for the preparation of the vWF-cp or vWF-cp fragment(s) and can be selected from eukaryotic and prokaryotic expression vectors. Examples of vectors for prokaryotic expression include plasmids such as pRSET, pET, pBAD, etc., wherein the promoters used in prokaryotic expression vectors include lac, trc, trp, recA, araBAD, etc. Examples of vectors for eukaryotic expression include: (i) for expression in yeast, vectors such as pAO, pPIC, pYES, pMET, using promoters such as AOX1, GAP, GAL1, AUG1, etc; (ii) for expression in insect cells, vectors such as pMT, pAcS, pIB, pMIB, pBAC, etc., using promoters such as PH, p10, MT, Ac5, OpIE2, gp64, polh, etc., and (iii) for expression in mammalian cells, vectors such as pSVL, pCMV, pRc/RSV, pcDNA3, pBPV, etc., and vectors derived form viral systems such as vaccinia virus, adeno-associated viruses, herpes viruses, retroviruses, etc., using promoters such as CMV, SV40, EF-1α, UbC, RSV, ADV, BPV, and β-Actin.

The vWF-cp fragment(s) can be selected from the group consisting of SEQ ID NOs1-6.

The vWF-cp fragments(s) can be peptides exhibiting amino acid sequences contained in the vWF-cp and having preferably at least 6 amino acids, more preferably from about 6 to about 50 amino acids. One advantage of using said peptides as a diagnostic reagent in the present invention is the selective determination of the specificity of the anti-vWF-cp antibody. The peptides can be produced by standard peptide synthesis techniques.

According to one embodiment of the invention, the vWF-cp or the vWF-cp fragment(s) are fused to a heterologous sequence. The heterologous sequence can be heterologous protein, polypeptide or peptide, in particular a functional peptide. The heterologous sequence can be a sequence having binding properties to a solid phase (e.g., the solid phase may have reactive site which allows covalent binding to the heterologous sequence, or has affinity to a carrier).

The heterologous protein, polypeptide or peptide can be selected from the group consisting of β-galactosidase, c-myc-product, glutathione S-transferase, FLAG-tags and derivatives thereof. The heterologous sequence can also comprise a series of several equal or different amino acids. Preferably, the heterologous sequence is a peptide that can form a covalent bond with the solid phase, or a polyhistidine that has high affinity, particularly to specific anti-poly-histidine antibodies. The heterologous sequence can be fused to vWF-cp or a vWF-cp fragment at either its N- or C-terminus. The heterologous sequence is typically fused to the C-terminal end of vWF-cp. The vWF-cp or a vWF-cp fragment is fused to the heterologous sequence such that the biological property of vWF-cp or a vWF-cp fragment is not negatively affected. A short peptide spacer may be inserted between the heterologous sequence and vWF-cp or a vWF-cp fragment, so as not to impede sterically the presentation of the epitopes of vWF-cp or the vWF-cp fragment.

According to one embodiment, the vWF-cp or a vWF-cp fragment is fused to a functional affinity peptide, in particular a peptide having several histidine residues, in some instances 3 to 20 histidine residues, and in other instances 6 to 15 histidine residues. The use of an affinity peptide in the form of poly-histidine (so called "His-tag") C-terminally fused to a protein for the purification of proteins has been described in EP 0 282 042.

The immobilization on the solid phase can be effected (e.g., directly or by covalent binding) via reactive groups of the solid phase and the heterologous sequence, or via a carrier having affinity to the heterologous sequence.

In one preferred embodiment of the invention, the heterologous sequence has high affinity to a carrier and the vWF-cp or vWF-cp fragment(s) are immobilized on the solid phase via the binding of its heterologous part to the carrier. Accordingly, the heterologous sequence has specific binding properties or high affinity to the carrier. According to one embodiment of the invention, the carrier is an antibody having affinity to the heterologous part of the vWF-cp fusion protein.

In one embodiment of the invention, vWF-cp or a vWF-cp fragment is fused to a poly histidine-tag as heterologous sequence and an anti-his-tag antibody is used as a carrier to immobilize vWF-cp or the vWF-cp fragment on a solid phase. Other heterologous affinity peptides and respective anti-affinity-peptide antibodies known to the person skilled in the art can also be used to immobilize the vWF-cp or vWF-cp fragment fusion protein.

The vWF-cp and/or vWF-cp fragment(s), or fusion proteins thereof, are immobilized on the solid phase separately on different spots, e.g. in different wells of a microtiter plate, wherein typically one defined antigen such as vWF-cp or a specific vWF-fragment is contained in one spot. With this assay system, the complete spectrum of anti-vWF-cp antibodies can be captured and anti-vWF-cp antibodies having specific binding activity within a region/domain of vWF-cp are identified. This is of major importance as by determination of anti-vWF-cp antibody specificity and determination of antigen binding site within the vWF-cp molecule the whole range of antibodies can be identified, and a specific treatment of patients having an anti-vWF-cp antibody associated disorder can be adapted, respectively. For example, anti-vWF-cp-antibodies can be selectively removed from the plasma of a patient identified to have specific anti-vWF-cp antibodies by subjecting the patient's plasma to affinity chromatography such as described herein which uses as an adsorbent specific vWF-cp fragments used in the assay and which have affinity to the antibody or antibodies. This allows for an improved treatment of patients having disorders associated with anti-vWF-cp antibodies compared to prior art methods.

According to one embodiment of the invention, the kit as described above further comprises as diagnostic agent an anti-vWF-cp antibody immobilized on the solid phase. The anti-vWF-cp antibody can be a monoclonal antibody derived by conventional hybridoma techniques or can be an antibody or antibody fragment obtained by recombinant technique, e.g., phage display or ribosome display. Such a set up in the kit of the present invention allows for differential diagnosis of thrombotic microangiopathic disorders. In particular, by providing a kit comprising immobilized vWF-cp, vWF-cp fragment(s) and anti-vWF-cp antibody on a solid phase the presence/absence of anti-vWF antibodies as well as the presence/absence of vWF-cp in a sample can be determined with one simple test system.

The present invention is also related to a method for determination of an anti-vWF-cp antibody in a sample, comprising the steps of providing vWF-cp and/or one or more vWF-cp fragment(s) immobilized on a solid phase without substantially impairing the biological property of the vWF-cp or vWF-cp fragment(s), contacting a biological sample of a patient suspected of having a disorder associated with the occurrence of anti-vWF-cp antibody with the immobilized vWF-cp and/or one or more vWF-cp fragments, and detecting a complex of anti-vWF-cp antibody/vWF-cp and/or anti-vWF-cp antibody/vWF-cp fragment(s).

The complex of anti-vWF-cp antibody/vWF-cp or anti-vWF-cp antibody/vWF-cp fragment(s) can be detected by methods well known in the art, e.g. by detection with a labelled antibody. The detection method can be selected from the group consisting of an enzyme assay, a chromogenic assay, a lumino assay, a fluorogenic assay, and a radioimmune assay. The reaction conditions to perform detection of the antibody/antigen-/complex formation depends upon the detection method selected. It is within the knowledge of the person skilled in the art to choose the optimal parameters, such as buffer system, temperature and pH for the respective detection system to be used.

The invention also relates to a method for differential diagnosis of thrombotic microangiopathic disorders with a kit as described above, wherein the kit comprises as diagnostic agent(s) either vWF-cp and/or one or more vWF-fragments, or vWF-cp and/or vWF-fragments and anti-vWF-cp antibodies, immobilized on a solid phase. The diagnostic agents are preferably each located on separate spots on the solid phase, e.g. in separate wells of a microtiter plate. This allows one to differentiate between samples comprising either vWF-cp or anti-vWF-cp antibodies or both by one assay system and to differentiate between thrombotic microangiopathic disorders, e.g. different forms of TTP or HUS.

The kit and method of the present invention can be used for diagnosis of a disorder associated with occurrence of anti-vWF-cp antibodies.

The kit and method of the present invention of the invention can also be used for diagnosis of different forms or disorders of thrombotic microangiopathy. The thrombotic microangiopathic (TM) disorder can be thrombotic thrombocytic purpura (TTP), neonatal thrombocytopenia, Henoch-Schönlein purpura, preclampsia, or hemolytic—uremic syndrome (HUS), HELLP syndrome, ARDS, peripheral digit ischemic syndrome, nonocclusive mesenteric ischemia, acute pancreatitis, acute hepatitis, purpura rheumatica, medicament-associated formation of thrombocytopenia, post-operative TM, cancer-associated TM, disseminated intravascular coagulation (DIC), systemic lupus erythematosus, liver cirrhosis, uremia, or acute inflammatory disorders.

The Examples provided herein clearly show that the presence of an anti-vWF-cp antibody in an acquired TTP patient, non-neutralizing in a standard vWF-cp activity assay but most likely impairing vWF-cp activity by mechanisms different from simply blocking substrate-cleaving activity, can be determined using a kit and a method of the present invention. This allows the fast and sensitive diagnosis of TTP and urgent needed life-saving clinical intervention, i.e. plasma treatment. The kit and the method of the present invention can be used for the differential diagnosis of various forms of TTP.

With the kit and the method of the present invention, all IgG classes as well as IgM antibodies can be detected, whereas prior art methods only allow detection of anti-vWF-cp antibodies of the IgG class.

The present invention will be further illustrated in the following examples, without any limitation thereto.

EXAMPLE 1

Construction of a vWF-cp and vWF-cp Fragment/His(6×)-tag

For expression of vWF-cp protein the vWF-cp cDNA clone as described in WO 02/42442 is used.

To construct a vWF-cp his-tag fusion, two consecutive PCRs are carried out to add the codons for 3× glycine, 6× histidines, stop and a XhoI restriction site.

PCR1: the wild-type full length pcDNA3.1.(+)/vWF-cp (ADAMTS13) as described in WO 02/42441 is used as template. With primers 7189 (5' GTG ATG GTG ATG GTG TCC ACC TCC GGT TCC TTC CTT TCC CTT CCA3') and 6526 (5' CTG CCT CGC CCG GAA CCC CA 3') a 1.3 kb fragment encompassing the C-terminal SgrAI/XhoI fragment from pcDNA3.1.(+)/vWF-cp is amplified. Using this fragment and primers 7190 (5' CCC TCT AGA CTC GAG TCA ATG GTG ATG GTG ATG GTG TCC ACC 3') and 6526, the second PCR is performed. The resulting product is purified, digested with SgrAI and XhoI, and used to replace the corresponding SgrAI/XhoI fragment in pcDNA3.1.(+)/vWF-cp wild-type construct.

Using the full length vWF-cp cDNA clone disclosed in WO 02/42442 as template, vWF-cp fragment constructs containing different fragments of the gene of the mature protein are generated by PCR using the following primer combinations (see also Table 4 of Primers and respective vWF-cp domain sequences).

E. coli Expression System: pBAD/Topo Thiofusion (Invitrogen)

| Fusion: Thioredoxin (N-terminal), 6xHis-tail (C-terminal) | | |
|---|---|---|
| DNA-fragment (bp) | protein-fragment (aa) | region in ADAMTS13 |
| 88-222 | 30(P)-74(R) | Propeptid |
| 223-1317 | 75(A)-439(E) | Cat./Disintegr./tsp1#1 |
| 1156-1317 | 386(R)-439(E) | Tsp1#1 |
| 1318-2055 | 440(K)-685(A) | Cys-rich/spacer |
| 2056-3393 | 686(W)-1131(V) | tsp1#2-8 |
| 3394-4281 | 1132(G)-1427(T) | Cub1 + 2 |

The PCR fragments are cut with suitable restriction enzymes and cloned into the vector such as pRSET (FIG. 1), and cleaved with the same enzymes resulting in the desired plasmids.

For construction of vWF-cp fragment(s)-his tag fusions, the vWF-cp fragments are modified according to construction of vWF-cp/his-tag as described above. The constructs are cloned with HIS-6 tag by substitution of the NdeI-XhoI fragment by the synthetic oligonucleotides o.pRET-FPdHIS(1)-6929 and o.pRSET-FPdHIS(2)-6930 (FIG. 1).

The vWF-cp, vWF-cp fragments or the respective his-tag fusions are recombinantly expressed in E. coli JM 109, purified and used for immobilization on a solid phase as described below.

HEK 293 Cell Clone Stably Expressing vWF-cp/C-His

HEK 293 (ATCC) cells are co-transfected with pcDNA3.1. (+)/vWF-cp/C-His and a selection plasmid harboring the hygromycine cassette using calcium phosphate precipitation. Initial clones and subsequent subclones are selected in culture medium supplemented with 100 µg/ml hygromycine and 800 µg/ml G418 (neomycinphosphotransferase encoded on pcDNA). Recombinant expressed vWF-cp/his—tag is purified and used for immobilization on a solid phase as described below.

EXAMPLE 2

Coupling of vWF-cp and/or vWF-cp Fragment(s) on a Carrier

Recombinant vWFcp, vWF-cp fragment(s) are either coupled directly on a solid phase, or via monoclonal anti-vWF-cp antibodies as carriers. vWF-cp-His-tag or vWF-cp fragment -His-tag are immobilized via an anti—His tag antibody on the surface of an ELISA plate. After incubation with a patient's plasma, anti-vWF-cp antibodies bound to vWF-cp or vWF-cp fragment are detected by a second antibody phosphatase conjugate recognizing the constant human antibody region. The phosphatase reacted with an appropriate substrate resulting in a chromogenic reaction and a yellow color. The intensity of the color is measured and the amount of antibody in the sample is determined by comparison with a standard curve comprising a known amount of anti-vWF antibody.

Figure 2B:
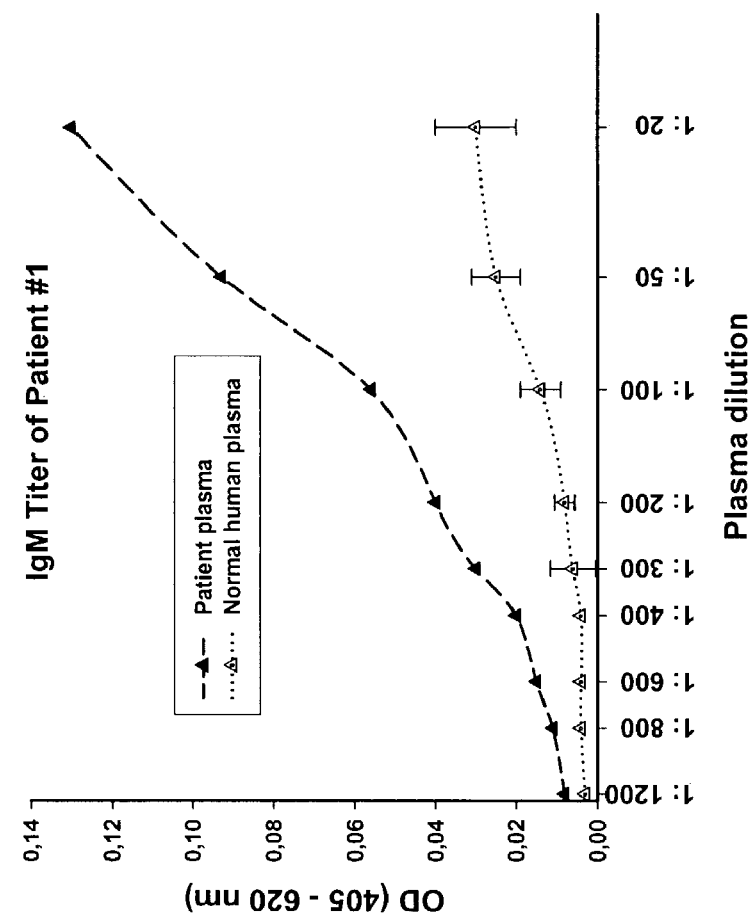
FIGS. 2A and 2B show the determination of IgG (FIG. 2A) and IgM (FIG. 2B) antibodies in plasma samples of a patient versus human normal plasma. The error bars indicate the two times added standard deviation of normal human plasma calculated from several plasma lots.
Figure 2A:
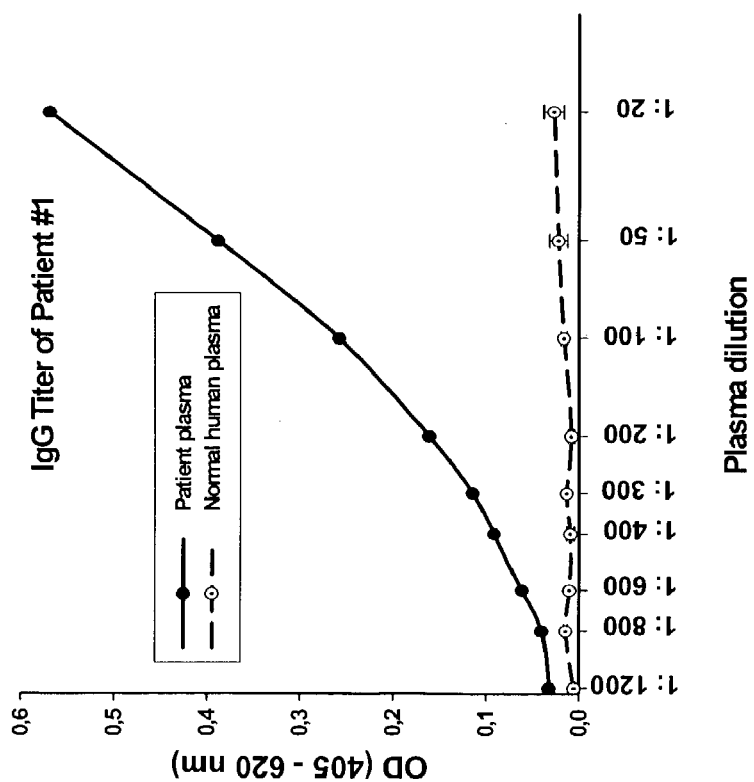

ELISA Setup:

A commercially available, BSA free, anti—His tag antibody ("carrier-antibody"; Qiagen, Germany) is diluted to a final concentration of 2 µg/mL in PBS pH 7.4. 100 µl per well is incubated for four hours at room temperature in a 96 well-microtiter plate. After three washing steps using PBST pH 7.4 (PBS buffer containing 0.1% (v/v) Tween 20), 250 µl of a blocking solution, containing PBS pH 7.4 and 2% (w/v) bovine serum albumin, are added and incubated at 4° C. over night to block all free binding sites. The solution is replaced by 100 µl of a recombinant vWF-cp—His tag labelled preparation. vWF-cp concentration is 1.5 µg/mL corresponding to 10 U/mL protease activity. vWF-cp samples are diluted to the final concentration in PBS 2% BSA. Due to the coated anti— His antibody recombinant vWFcp/his-tag is captured and immobilized via the carrier antibody. After two hours at room temperature, ten washing steps follow. The washing buffer contains PBS pH7.4 and 0.1% (v/v) Tween 20. Plasma samples of patients are diluted 1:20, 1:50, 1:100, 1:200, 1:300, 1:400, 1:600, 1:800 and 1:1200 in PBS pH 7.4 containing 2% BSA and 100 µl of each dilution is incubated at room temperature for 3 hours on the recombinant vWF-cp-containing wells. Inhibitory antibodies are bound on the surface of the immobilized vWF-cp and unbound antibodies are washed away by ten washing steps using PBST pH 7.4. Detection of human antibodies is performed with a mouse anti-human IgG Fc specific antibody or mouse anti-human IgM antibody, alkaline phosphatase conjugated. The antibody is diluted 1:60000 in PBS 2% BSA to the final working solution and incubated for 2 hours at room temperature (100 µl/well), followed by ten washing steps with PBST pH 7.4. Addition of an alkaline phosphatase substrate (PNPP) results in a yellow color, whereby the color intensity reflects the amount of bound antibody (antibody/vWF-cp). The color intensity is measured in an ELISA reader and the amount of antibody within the plasma sample is calculated in reference to a standard curve of NP by serial dilution. As negative control, dilutions of normal human plasma (NHP) are treated accordingly. The results are presented in FIGS. 2A and 2B. The results show that human anti-vWF-cp antibodies in a patients can be clearly detected in at least a plasma dilution of 1:600.

Normal human plasma is used as control and the standard deviation (SD) calculated for several plasma lots. Antibody titres above that of normal human plasma+2 SD are evaluated as positive.

Analysis of TTP Patient Samples

Samples from patients with TTP and normal plasma samples are subjected to ELISA comprising immobilized vWF-cp. The results are shown in Table 1. Patient 1 has an IgG titer of 1:600 and an IgM titer of 1:400. The IgG titer of patient 2 is much higher (1:1200) while the IgM titer is only 1:100. Patient 1 suffers from an acute TTP, while patient 2 is in remission after TTP. Patient 1 shows no inhibitory titer, whereas patient 2 has an inhibitory titer of about 60 U/mL. Normal human plasma shows no reaction.

TABLE 1

Anti-vWF-cp antibody detection ELISA. IgG as well as IgM titers of two patients.

|  | 1:20 | 1:50 | 1:100 | 1:200 | 1:300 | 1:400 | 1:600 | 1:800 | 1:1200 |
|---|---|---|---|---|---|---|---|---|---|
| IgG#1 | + + + + | + + + + | + + + | + + + | + + | + + | + | − | − |
| IgM#1 | + + + | + + + | + + + | + + | + + | + | − | − | − |
| NP | − | − | − | − | − | − | − | − | − |
| IgG#2 | + + + + | + + + + | + + + + | + + + | + + + | + + + | + + | + + | + |
| IgM#2 | + + | + + | + | − | − | − | − | − | − |
| NP | − | − | − | − | − | − | − | − | − |

Samples of patients with TTP and normal plasma samples are subjected to ELISA comprising immobilized vWF-cp fragments derived from different regions of vWF-cp. The results are shown in Table 2. IgGs and IgMs of patient #1 (no inhibitory titer) show binding of antibodies on domains trombospondin 2-8 and the Cub domains. IgGs and IgMs of patient #2 show binding on the catalytic domain, which is consistent to the inhibitory titer. Normal human plasma does not react with any domain. Patient's plasma is tested in duplicates and two different plasma dilutions (1:50 and 1:100).

TABLE 2

Analysis of the binding on different ADAMTS-13 fragments of patient's antibodies

|  | Catalytic domain, 1:50 | Catalytic domain, 1:100 | Catalytic, disintegrin, tsp1 1:50 | Catalytic, disintegrin, tsp1 1:100 | Cys-rich, spacer, 1:50 | Cys-rich, spacer, 1:100 | Tsp 2-8, 1:50 | Tsp 2-8, 1:100 | CUB 1 + 2 1:50 | CUB 1 + 2 1:100 |
|---|---|---|---|---|---|---|---|---|---|---|
| IgG#1 | − | − | − | − | − | − | + + | + | + | − |
| IgM#1 | − | − | − | − | − | − | + + | + | + | − |
| NP | − | − | − | − | − | − | − | − | − | − |
| IgG#2 | + + + + | + + + | + + | + + | − | − | − | − | − | − |
| IgM#2 | + + | + + | + | − | − | − | − | − | − | − |
| NP | − | − | − | − | − | − | − | − | − | − |

Samples of patients with TTP and from normal plasma are subjected to ELISA comprising immobilized anti-vWF-cp antibody. The results are shown in Table 3.

ADAMTS-13 levels of patients #1 and #2 can be clearly detected; normal human plasma shows the same levels. Patient #3 is being characterized to carry a genetic defect on one allele causing a 50% reduced activity. A 50% reduction on protein amount can also be seen in our assay system. Patient #4 is being characterized to completely lack ADAMTS-13 protein due to a homozygous nonsense mutation. Consequently, no protein could be detected.

TABLE 3

Detection of ADAMTS-13 levels in plasma using anti-vWF-cp antibodies for capturing.

|  | 1:20 | 1:50 | 1:100 | 1:200 | 1:300 | 1:400 | 1:600 | 1:800 | 1:1200 |
|---|---|---|---|---|---|---|---|---|---|
| ADAMTS-13 #1 | + + + + | + + + + | + + + + | + + + | + + + | + + + | + + | + | − |
| ADAMTS-13 #2 | + + + + | + + + + | + + + + | + + + | + + + | + + + | + + | + | − |
| ADAMTS-13 #3 | + + + | + + + | + + + | + + | + + | + | − | − | − |
| ADAMTS-13 #4 | − | − | − | − | − | − | − | − | − |
| NP | + + + + | + + + + | + + + + | + + + | + + + | + + + | + + | + | − |

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

TABLE 4

| PRIMER (Baxter #) | DNA sequence (5' → 3') | ADAMTS-13 DOMAIN | PRIMARY SEQUENCE |
|---|---|---|---|
| 7442 (dp) | CCCTCCCATTTCCAGCAGAGTTGTCTT | Propeptid | SEQ ID. 1: PSHFQQSCLQALEPQAVSSYLSPGAPLKGRPPSPGFQRQRQRQRR |
| 7443 (rp) | CCGCCTCTGCCTCTGCCTCTG | | |
| 7359 (rp) | CTCGCAGGCCTGAGTGTTGCACATCTC | Catalytic/ disintegrin/ Tsp-1/#1 | SEQ ID. 2: AAGGILHLELLVAVGPDVFQAHQEDTERYVLTNLNIGAELLRDPSLG AQFRVHLVKMVILTEPEGAPNITANLTSSLLSVCGWSQTINPEDD TDPGHADLVLYITRFKLEDPDGNRQVRGVTQLGGACSPTWSCLIT EDTGFDLGCTIAHEIGHSFGLEHDGAPGSGCGPSGHVMASDGAA PRAGLAWSPCSRRQLLSLLSAGRARCVWDPPRPQPGSAGHPPD AQPGLYYSANEQCRVAFGPKAVACTFAREHLDMCQALSCHTDPL DQSSCSRLLVPLLDGTECGVEKWCSKGRCRSLVELTPIAAVHG RWSSWGPRSPCSRSCGGGVVTPPPQCNNPRPAFGGRACVGAD LQAEMCNTQACE |
| 7360 (dp) | GCTGCAGGCGGCATCCTACACCTG | | |
| 7600 (dp) | CGCTGGTCTAGCTGGGGTCCC | Tsp-1//#1 | SEQ ID. 3: RWSSWGPRSPCSRSCGGGVVTPPPQCNNPRPAFGGRACVGAD LQAEMCNTQACE |
| 7601 (rp) | CTCGCAGGCCTGAGTGTTGCA | | |
| 7357 (rp) | GGCCTGCCGTGGCTTAGGCTGGAAGTA | Cystein-rich/ spacer | SEQ ID. 4: KTQLEFMSQQCARTDCQPLRSSPGGASFYHWGAAVPHSQGDAL CRHMCRAIGESFIMKRGDSFLDGTRCMPSGPREDGTLSLCVSGS CRTFGCDCRMDSQQVWDRCQVCGGDNSTC SPRKGSFTAGRAREYCTFLTCTPNLTSCYIANHRPLFTHLAVRIGG RYVVAGKMSISPNTTYPSILLEDGRVEYRVALTEDRLPRLEEIRIW GPLQEDADIQVYRRYGEEYGNLTRPDITFTYFQPKPRQA |
| 7358 (dp) | AAGACCCAGCTGGAGTTCATGTCGCAA | | |
| 7441 (dp) | TGGGTGTGGGCCGCTGTGCGT | Tsp-1/ #2-8 | SEQ ID. 5: WVWAAVRGPCSVSSGAGLRWVNQSCLDQARKELVETVQCQGSQQPPA WPEACVLEPCPPYWAVGDFGPCSASCGGGLRERPVRCVEAQGSLLKT LPPARCRAGAQQPAVALETCNPQPCPARWEVSEPSSCTSAGGAGLAL ENETCVPGADGLEAPVTEGPGSVDEKLPAPEPCVGMSCPPGWGHLDA TSAGEKAPSPWGSIRTGAQAAHVWTPVAGSCSVSCGRGLMELRFLCM DSALRVPVQEELCGLASKPGSRREVCQAVPCPARWQYKLAACSVSCG RGVVRRILYCARAHGEDDGEEILLDTQCQGLPRPEPQEACSLEPCPP |

TABLE 4-continued

| PRIMER (Baxter #) | DNA sequence (5' → 3') | ADAMTS-13 DOMAIN | PRIMARY SEQUENCE |
|---|---|---|---|
| | | | RWKVMSLGPCSASCGLGTARRSVACVQLDQGQDVEVDEACAALVRPE |
| | | | ASVPCLIADCTYRWHVGWMECSVSCGDGIQRRRDTCLGPQAQAPVPA |
| 7444 (rp) | CACACAGGGCCCAGCCCAGCA | | DFCQHLPKPVTVRGCWAGPCV |
| 7439 (dp) | GGACAGGGTACGCCCAGCCTG | Cub 1+2 | SEQ ID. 6: |
| | | | GQGTPSLVPHEEAAAPGRTTATPAGASLEWSQARGLLFSPARQPRRL |
| | | | LPGPQENSVQSSACGRQHLEPTGTIDMRGPCQADCAVAIGR |
| | | | PLGEVVTLRVLESSLNCSAGDMLLLWGRLTRKMCRKLLDMTFSSK |
| | | | TNTLVVRQRCGRPGGGVLLRYGSQLAPETFYRECDMQLFGPWG |
| | | | EIVSPSLSPATSNAGGCRLFINVAPHARIAIHALATNMGAGTEGANA |
| | | | SYILIRDTHSLRTTAFHGQQVLYWESESSQAEMEFSEGFLKAQALRG |
| | | | QYWTLQSWVPEMQDPQSWKGKEGT |
| 7440 (rp) | GGTTCCTTCCTTTCCCTTCCAGGACTG | | |

We claim:

1. A method for detecting an anti-von Willebrand Factor-cleaving protease ("anti-vWF-cp") antibody in a sample, where the antibody binds to a catalytic domain, a thrombospondin 2-8 domain, or a Cub domain of a vWF cp fragment, comprising the steps of
   (a) providing a solid phase comprising an immobilized vWF-cp fragment fused to a heterologous sequence that is separated from the vWF-cp fragment by a spacer, wherein the biological property of said vWF-cp fragment is not substantially impaired and the presentation of the epitopes of the vWF-cp fragment is not sterically impeded, and further, wherein the vWF-cp fragment comprises the catalytic domain, the thrombospondin 2-8 domain, or the Cub domain;
   (b) contacting a biological sample of a patient suspected of having thrombotic thrombocytopenic purpura (TTP) associated with occurrence of the anti-vWF-cp antibody with said immobilized vWF-cp fragment; and
   (c) detecting a complex of the anti-vWF-cp antibody and the vWF-cp fragment, wherein the presence of a complex with the catalytic domain is indicative of the presence of inhibitory antibodies that impair the catalytic function of substrate cleavage and the presence of a complex with the thrombospondin 2-8 domain or the cub domain is indicative of the presence of antibodies that do not inhibit substrate cleavage.

2. The method according to claim 1, wherein the solid phase is selected from the group consisting of plates, membranes, paper, film, strips, and pearls.

3. The method according to claim 1, wherein said complex is detected by an assay selected from the group consisting of an enzyme assay, a chromogenic assay, a lumino assay, a fluorogenic assay, and a radioimmune assay.

4. A method for diagnosis of thrombotic thrombocytopenic purpura (TTP) in a patient having or suspected of having, a form of TTP comprising the steps of
   (a) providing a solid phase comprising immobilized vWF-cp fragment fused to a heterologous sequence that is separated from the vWF-cp fragment by a spacer, wherein the biological property of said vWF-cp fragment is not substantially impaired and the presentation of the epitopes of the vWF-cp fragment is not sterically impeded, and further, wherein the vWF-cp fragment comprises a catalytic domain, a thrombospondin 2-8 domain, or a Cub domain;
   (b) contacting a biological sample of a patient suspected of having TTP associated with occurrence of an anti-vWF-cp antibody with said immobilized vWF-cp fragment;
   (c) detecting formation of a complex of the anti-vWF-cp antibody and immobilized vWF-cp fragment, thereby diagnosing and/or discriminating between different forms of TTP, wherein the presence of a complex with the catalytic domain is indicative of the presence of inhibitory antibodies that impair the catalytic function of substrate cleavage and the presence of a complex with the thrombospondin 2-8 domain or the cub domain is indicative of the presence of antibodies that do not inhibit substrate cleavage; and (d) determining a vWF-cp level in a plasma sample from the patient and comparing the vWF-cp level in the plasma sample with a level of vWF-cp in a sample of normal plasma, wherein the detection of the complex of anti-vWF-cp antibody from the biological sample and immobilized vWF-cp fragment, and determination of a vWF-cp level in the plasma sample from the patient that is the same as the level in normal plasma indicates that the form of TTP is acquired TTP.

5. The method according to claim 4, wherein said solid phase in step (a) further comprises an immobilized anti-vWF-cp antibody.

6. The method according to claim 1 wherein the vWF-cp fragment is the catalytic domain, the thrombospondin 2-8 domain, or the Cub domain.

7. The method according to claim 4, wherein the vWF-cp fragment is the catalytic domain, the thrombospondin 2-8 domain or the Cub domain.

* * * * *